(12) United States Patent
Mokelke et al.

(10) Patent No.: US 8,781,586 B2
(45) Date of Patent: Jul. 15, 2014

(54) HEMOSTASIS VALVE AND GUIDEWIRE PACING SYSTEM

(71) Applicant: Cardiac Pacemakers, Inc., St. Paul, MN (US)

(72) Inventors: Eric A. Mokelke, White Bear Lake, MN (US); Allan C. Shuros, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 19 days.

(21) Appl. No.: 13/777,421

(22) Filed: Feb. 26, 2013

(65) Prior Publication Data
US 2013/0172924 A1    Jul. 4, 2013

Related U.S. Application Data

(62) Division of application No. 12/422,770, filed on Apr. 13, 2009, now Pat. No. 8,412,329.

(60) Provisional application No. 61/047,215, filed on Apr. 23, 2008.

(51) Int. Cl.
| | |
|---|---|
| *A61N 1/00* | (2006.01) |
| *A61M 31/00* | (2006.01) |
| *A61M 25/16* | (2006.01) |
| *A61M 25/18* | (2006.01) |
| *A61M 25/10* | (2013.01) |
| *A61M 39/06* | (2006.01) |
| *A61N 1/05* | (2006.01) |
| *A61M 39/10* | (2006.01) |

(52) U.S. Cl.
CPC ........... *A61N 1/0565* (2013.01); *A61M 25/104* (2013.01); *A61M 39/0606* (2013.01); *A61M 2039/062* (2013.01); *A61M 2039/1022* (2013.01); *A61N 1/056* (2013.01); *A61N 2001/0585* (2013.01); *A61M 2039/0633* (2013.01)

USPC ............ 607/32; 607/116; 607/122; 604/510; 604/533

(58) Field of Classification Search
USPC ..................... 607/32, 116, 122; 604/510, 533
See application file for complete search history.

(56) References Cited

U.S. PATENT DOCUMENTS

| | | |
|---|---|---|
| 5,059,186 A | 10/1991 | Yamamoto et al. |
| 5,203,776 A | 4/1993 | Durfee |

(Continued)

FOREIGN PATENT DOCUMENTS

WO    WO2004010853 A2    2/2004

OTHER PUBLICATIONS

International Search Report and Written Opinion issued in PCT/US2009/040374, mailed Oct. 19, 2009, 20 pages.

(Continued)

*Primary Examiner* — Joseph Stoklosa
*Assistant Examiner* — Lindsey G Hankins
(74) *Attorney, Agent, or Firm* — Faegre Baker Daniels LLP (57) ABSTRACT

Systems and methods for temporarily pacing a patient's heart are provided. One system includes a hemostasis valve with an adjustable electrical connection, the adjustable electrical connection having one or more adjustable contacts. The adjustable contacts have a first, radially expanded configuration and a second, radially constricted configuration. In the radially constricted configuration, the adjustable contacts are configured to pierce through a layer of an elongate medical device that is disposed in the hemostasis valve. The elongate medical device has a distal electrode and a conductor extending along a portion of the elongate medical device. The adjustable contacts pierce through a make contact with the conductor, providing an electrical pathway to the distal electrode. Also provided are vascular access systems including a hemostasis valve and a guide catheter, guide wire torquers with adjustable contacts and methods of temporarily pacing a patient's heart.

5 Claims, 10 Drawing Sheets (56) References Cited

U.S. PATENT DOCUMENTS

| | | | |
|---|---|---|---|
| 5,772,642 | A | 6/1998 | Ciamacco, Jr. et al. |
| 5,876,385 | A | 3/1999 | Ikari et al. |
| 6,723,083 | B2 | 4/2004 | Kiemeneij |
| 7,150,737 | B2 | 12/2006 | Purdy et al. |
| 8,412,329 | B2 | 4/2013 | Mokelke et al. |
| 2002/0002352 | A1 | 1/2002 | Becker et al. |
| 2005/0137665 | A1 | 6/2005 | Cole |
| 2006/0178666 | A1 | 8/2006 | Cosman et al. |
| 2006/0241704 | A1 | 10/2006 | Shuros et al. |
| 2006/0259087 | A1 | 11/2006 | Baynham et al. |
| 2009/0270941 | A1 | 10/2009 | Mokelke et al. |

OTHER PUBLICATIONS

Invitation to Pay Additional Fees and, Where Applicable, Protest Fee and Partial Search Report, issued in PCT/US2009/040374, mailed Jul. 27, 2009, 7 pages.

Staat, Patrick et al., "Postconditioning the Human Heart", Journal of the American Heart Association, Circulation 2005, vol. 112, pp. 2143-2148.

Vanagt, et al., Pacing-Induced Dyssynchrony During Early Reperfusion Reduces Infarct Size, Journal of the American College of Cardiology, vol. 49, No. 17, 2007, pp. 1813-1819.

HEMOSTASIS VALVE AND GUIDEWIRE PACING SYSTEM

CROSS-REFERENCE TO RELATED APPLICATION

This application is a divisional application of U.S. application Ser. No. 12/422,770, filed Apr. 13, 2009, entitled "Hemostasis Valve And Guidewire Pacing System" which claims the benefit of Provisional Application No. 61/047,215, filed Apr. 23, 2008, entitled "Hemostatis Valve and Guidewire Pacing System" both of which are herein incorporated by reference in their entirety.

BACKGROUND

Cardiac pacing is performed on patients for a variety of reasons. In some procedures, the heart rhythm of a patient is monitored and/or managed by devices that are temporarily placed in a patient. Temporary pacing is often performed prior to, during and/or after performing a procedure on the heart. For example, pacing can be performed prior to, during and/or after a revascularization procedure is performed on the heart. There exists a need for alternative designs and methods for temporarily pacing a patient's heart.

SUMMARY

In one embodiment of the invention, a hemostasis valve comprises a valve body including a proximal port and a distal port and the valve body defines a lumen extending between the proximal and distal ports. A valve is disposed in the lumen and the valve includes a resilient material defining an opening. The resilient material is configured to deform and form a seal around a medical device that extends through the opening. In addition, an adjustable electrical contact is disposed in the lumen of the valve body and has an electrically conductive surface. The adjustable electrical contact has an expanded configuration and a constricted configuration. In the expanded configuration, the electrically conductive surface is positioned at a first radial position and in the constricted configuration, the electrically conductive surface is positioned at a second radial position, the second radial position being radially inward of the first radial position.

In another embodiment of the invention, a torque device comprises an inner member defining a lumen one or more adjustable contacts disposed in the lumen. The adjustable contacts have an expanded configuration and a constricted configuration. In addition, an outer member is disposed on the inner member and the outer member has a first configuration and a second configuration, wherein moving the outer member from the first to the second configuration provides a compressive force on the inner member, which moves the adjustable contacts from the expanded to the constricted configuration. Further, an electrical conductor extends from an outer surface of the torque device to the one or more contacts.

In another embodiment of the invention, a vascular access system comprises a hemostasis valve including a valve body defining a passageway between proximal and distal ports. A valve and an adjustable electrical contact are disposed in the passageway. The vascular access system also has a first connector member disposed adjacent the distal port of the valve body. Further, a guide catheter includes an elongate shaft, an electrode disposed on a distal portion of the shaft and a second connector member disposed on the shaft adjacent a proximal end of the shaft, wherein the first and second connectors are configured to mechanically and electrically couple to one another.

In another embodiment of the invention, a vascular access system comprises a guide catheter having a distal portion and a proximal end, an electrode disposed on the distal portion, a first electrical contact disposed on the proximal end, a first lumen extending between the distal portion and the proximal end, and a first conductor extending between the electrode and the first electrical contact. The vascular access system also includes a hemostasis valve having a valve body with a distal end and a proximal end, a second lumen extending between the distal and proximal ends, a valve disposed in the lumen, a second electrical contact disposed on the distal end and a second conductor connecting the second electrical contact with a proximal portion of the valve body. The guide catheter proximal end and the hemostasis valve distal end are removably connected to one another and the first and second electrical contacts are electrically coupled to one another, forming an electrical pathway between the hemostasis valve and the electrode. Further, the first and second lumens are fluidly connected to one another, forming a fluid pathway and the fluid pathway is fluidly and electrically isolated from the first and second conductors, the first and second electrical contacts and the electrode.

In yet another embodiment of the invention, a method of providing temporary cardioprotective pacing comprises providing any of the hemostasis valves described herein. A therapeutic system is disposed through the hemostasis valve. The therapeutic system comprises one or more distal electrodes and a conductive element electrically coupled to the one or more electrodes and extending along a portion of the therapeutic system. A valve portion of the hemostasis valve is sized and configured to seal around the portion of the therapeutic system that extends through the hemostasis valve. The distal portion of the therapeutic system is disposed in a cardiac artery and an adjustable electrical contact within the hemostasis valve is moved from an expanded configuration to a constricted configuration, piercing an outer layer of the therapeutic system and making electrical contact with a conductive element of the therapeutic system. Cardioprotective pacing signals are provided through the hemostasis valve to the electrode.

While multiple embodiments are disclosed, still other embodiments of the present invention will become apparent to those skilled in the art from the following detailed description, which shows and describes illustrative embodiments of the invention.

Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
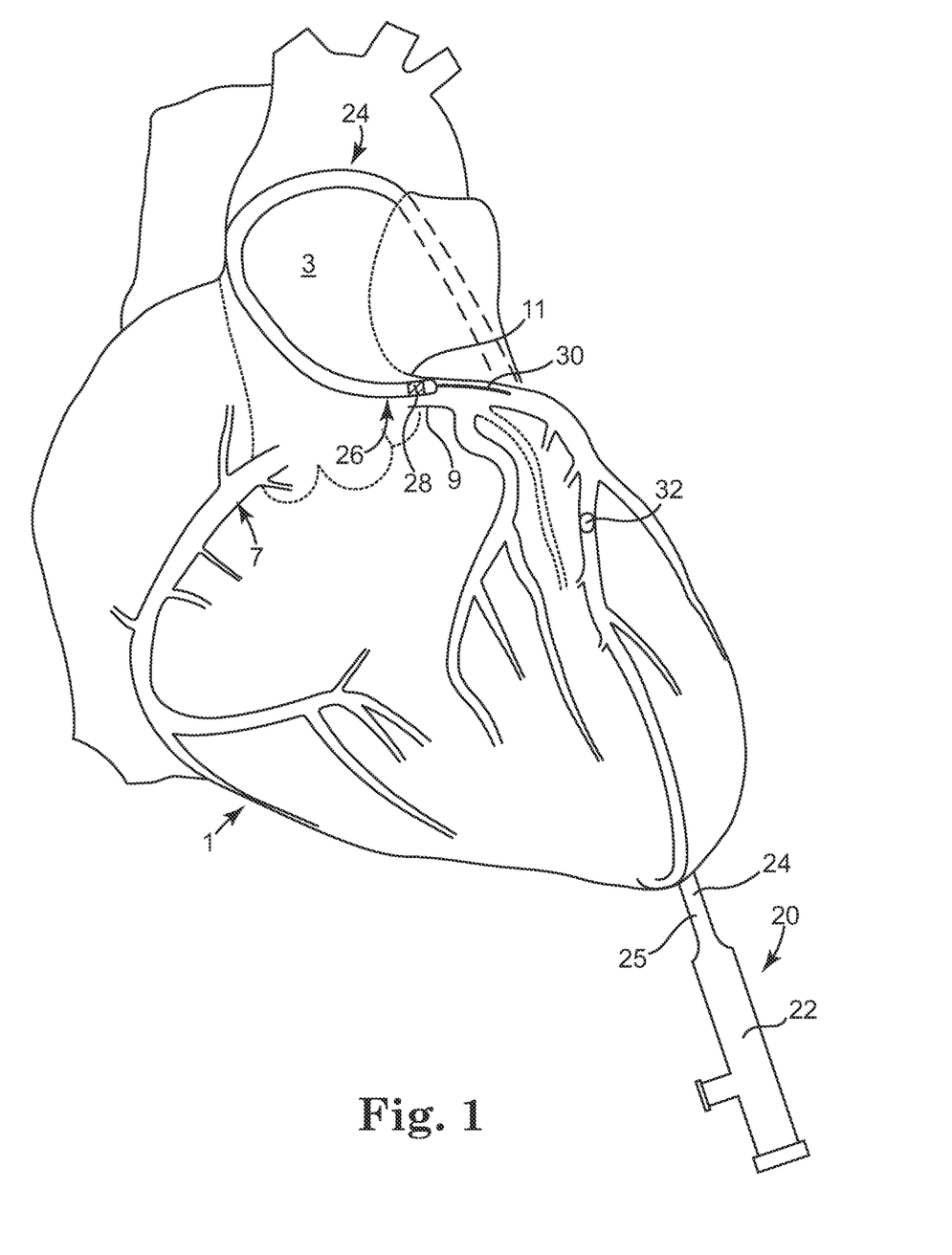
FIG. 1 is a human heart with the aorta and several of the coronary arteries shown in a cut away view and a portion of a guide catheter disposed in the aorta according to some embodiments of the present invention.

FIG. 1 shows a human heart 1 with an aorta 3 and several coronary arteries 7, 9. An ostium 11 allows blood to flow from the aorta 3 into the left main coronary artery 9. A vascular access system 20 comprises a hemostasis valve 22 and a guide catheter 24. The guide catheter 24 has a proximal portion 25 and a distal portion 26. The guide catheter distal portion 26 has an electrode 28 disposed thereon, and the distal portion 26 extends through the aortic arch and into the ostium 11. A variety of different catheter shapes are available which generally facilitate access to the coronary ostium. For example, see U.S. Pat. No. 5,203,776, issued on Apr. 20, 1993 to Durfee, U.S. Pat. No. 5,876,385, issued on Mar. 2, 1999 to Ikari et al. and U.S. Pat. No. 6,723,083, issued on Apr. 20, 2004 to Keimeneij, all of which are incorporated herein by reference in their entirety.

As shown in FIG. 1, branches form off of the main coronary arteries 7, 9 to supply oxygenated blood to the various parts of the heart. A blockage 32 is shown in a branch of the left coronary artery 9. The blockage 32 can be caused by an embolus, a thrombus, or by other types of materials. In some instances, the partial or complete blockage of the flow of blood through an artery causes ischemia, and possibly eventually an infarction, in a portion of the heart. (Hereinafter, ischemia and infarction in the heart will collectively be referred to as myocardial infarction, or "MI").

A variety of options are available for treating a MI. For example, some treatment options break up the blockage 32 to that it can flow through the arterial system, some treatment options displace the blockage 32, and some treatments capture and remove the blockage 32. Specific methods for revascularizing the coronary arteries will be further discussed below. Once the artery has been revascularized, blood flows through the artery to the affected area of the heart. This reintroduction of blood flow is called reperfusion.

The hemostasis valve 22 and at least a portion of the guide catheter proximal portion 25 are disposed outside the body and the guide catheter 24 extends through a patient's vasculature to the aorta. For example, in some embodiments the guide catheter 24 accesses the body through the femoral artery. In some embodiments, the vascular access system 20 also includes a therapeutic system 30, which is shown in FIG. 1 extending from the guide catheter distal portion 26. As further explained below, the therapeutic system 30 can be a guidewire, a therapy catheter, a combination of a guidewire and a therapy catheter, or another therapeutic device.

It has been found that pacing the heart can in some cases have a protective effect on those portions of the heart. In some embodiments, the portion of the heart being paced is the portion of the heart being repurfused and in other embodiments the portion of the heart being paced is a portion of the heart other than the portion being repurfused. Such cardioprotective pacing is described, for example, in U.S. Patent Publication No. 2006/0241704 and U.S. Patent Publication No. 2006/0259087, both of which are herein incorporated by reference in their entirety.

Figure 2:
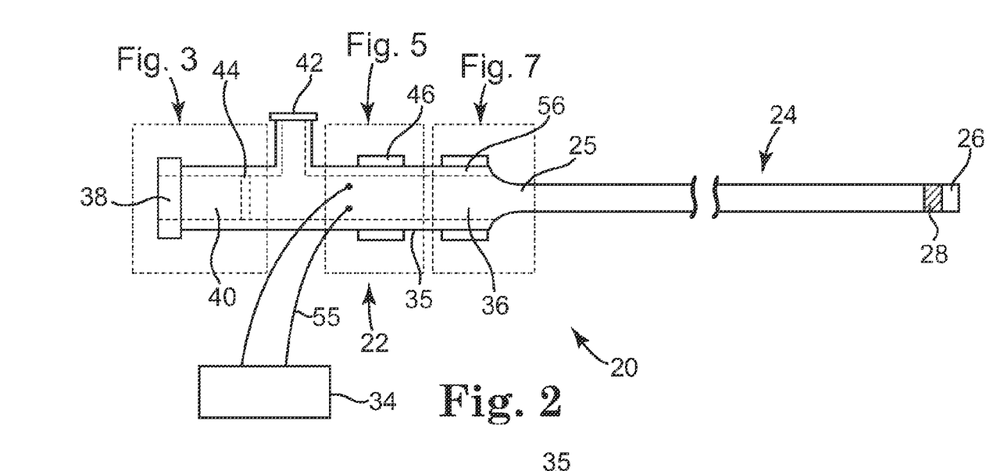
FIG. 2 is a perspective view of a vascular access system according to some embodiments of the present invention.

FIG. 2 shows a pacing-capable vascular access system 20 according to some embodiments of the invention. The vascular access system 20 includes a hemostasis valve 22, guide catheter 24 and a pacing system controller 34. The hemostasis valve 22 has a valve body 35 with a distal end 36 defining a distal port and a proximal end 38 defining a proximal port. The valve body 35 forms a lumen or passageway 40 between the distal and proximal ports. A side access port 42 is optionally provided on the valve body 35 in order to provide access for procedures such as injecting drugs, contrast agents or other substances into a patient through the hemostasis valve 22. In some embodiments, the side port 42 is adapted to electrically connect to a tubing or other elongate device wherein the tubing or other elongate device has a conductor for supplying electrical energy to the hemostasis valve. The tubing or other elongate device can supply electrical signals to the hemostasis valve in place of, or in addition to, other electrical conductors (e.g., wires 55, as discussed below). The hemostasis valve 22 also has a valve 44 and an adjustable electrical contact 46, both of which will be further described below.

As mentioned above, the guide catheter 20 has a proximal portion 25, a distal portion 26 with an electrode 28. A connector member 56, which is shown in more detail in FIGS. 7-9, removably connects the guide catheter proximal portion 25 to the hemostasis valve body distal end 36.

The vascular access system 20 also has one or more wires 55 electrically coupling the controller 34 to the hemostasis valve 22. As is further discussed below, electrical signals can pass to or from the controller 34, through the wires 55, through the hemostasis valve 22 and the guide catheter 24, to or from the electrode 28.

In addition, as shown generally in FIG. 1 and in greater detail below, the therapeutic system 30 is passed through the hemostasis valve 22 and the guide catheter 24. The therapeutic system 30 optionally has one or more electrodes disposed on a distal portion of the therapeutic system 30. As discussed below, in some embodiments the adjustable electrical contact 46 facilitates electrical connection between the hemostasis valve 22 and the therapeutic system 30. Electrical signals can pass to or from the controller 34, through the wires 55 and through the hemostasis valve 22 and the therapeutic system 30, to or from the one or more electrodes at the distal end of the therapeutic system 30.

The electrodes disposed on the guide catheter and the therapeutic device facilitate temporary pacing before, during or after a procedure is performed on the heart. For example, before, during or after a revascularization procedure, a portion of the heart is provided with cardioprotective pacing. Examples of such procedures will be described below.

Figure 3:
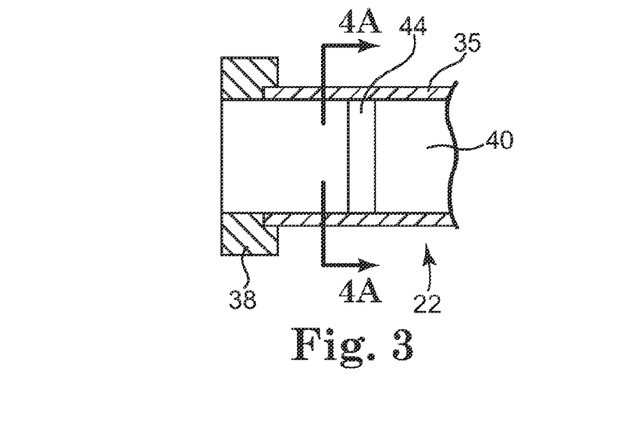
FIG. 3 is a longitudinal cross-section of a valve portion of the vascular access system of FIG. 2 according to some embodiments of the present invention.

A proximal portion of the hemostasis valve of FIG. 2 is shown in FIG. 3. The hemostasis valve body 35 defines the lumen or passageway 40, and the valve 44 is disposed in the lumen 40. The valve 44 comprises a resilient material (e.g., a silicon, a rubber, or any other suitable resilient material), and an opening is formed in the resilient material. An elongate medical device (e.g., one or more portions of the therapeutic system 30) can be passed through the hemostasis valve body 35 and through the opening defined in the resilient material.

Figure 4A:
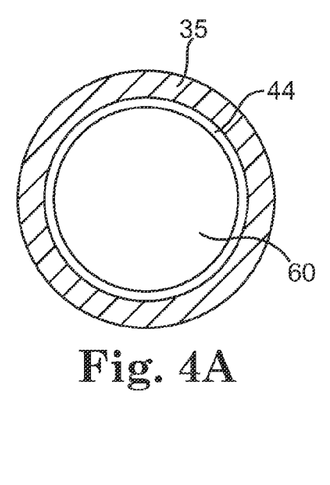
FIG. 4A is a cross-section of the valve portion of FIG. 3 according to some embodiments of the present invention.

FIG. 4A shows an end view of the valve 44 according to some embodiments of the invention. The valve 44 is disposed within the hemostasis valve body 35. The valve 44 has an opening 60 formed therethrough, the opening 60 sized slightly smaller than the elongate medical device that is being passed through the hemostasis valve. As the medical device is passed through the valve 44, the resilient material deforms radially outwardly, allowing the medical device to pass through the valve while also forming a complete or partial seal around the elongate medical device. This seal around the elongate medical device completely or partially prevents body fluids (e.g., blood) from flowing back through the hemostasis valve lumen 40 around the elongate medical device. Prior to the elongate medical device being passed through the valve 44, and after the medical device is removed from the valve 44, the opening 60 remains open.

Figure 4B:
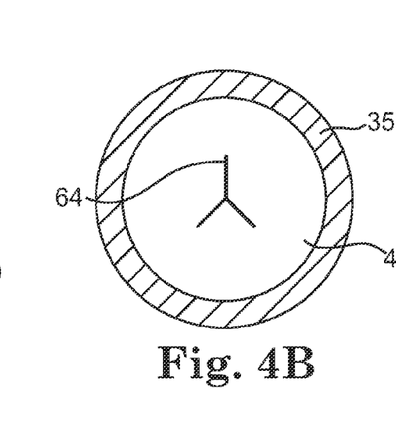
FIG. 4B is a cross-section of another valve structure according to some embodiments of the present invention.

FIG. 4B shows an end view of a valve 44' according to embodiments of the present invention. The valve 44' is disposed within the hemostasis valve body 35, and an opening is formed in the valve 44' by one or more slits 64. The valve 44' comprises a resilient material (e.g., silicon, rubber, or any other suitable resilient material). The elongate medical device can be passed through the opening formed by the slits 64, and the resilient material deforms to allow the medical device to pass through the valve 44' while the valve 44' seals around the medical device, completely or partially preventing the flow of fluids (e.g., blood) back through the hemostasis valve lumen 40 around the elongate medical device.

In some embodiments, the valve 44' is self-sealing. For example, before the medical device is inserted through the valve 44', and after the medical device is removed from the valve 44', the valve 44' completely or partially prevents the free flow of body fluids out of a patient's body through the hemostasis valve 22. In addition, any other valve structure that will allow passage of, and provide a partial or complete seal around, the elongate medical device can be used in place of the valves 44, 44' described herein. For example, a valve could be disposed inside of a compression fitting (e.g., a compression fitting similar to the compression mechanism shown in FIG. 5 and described further below). The compression fitting could cause the valve material to be compressed, making contact with, and sealing around, a therapeutic device being passed through the hemostasis valve.

Figure 5:
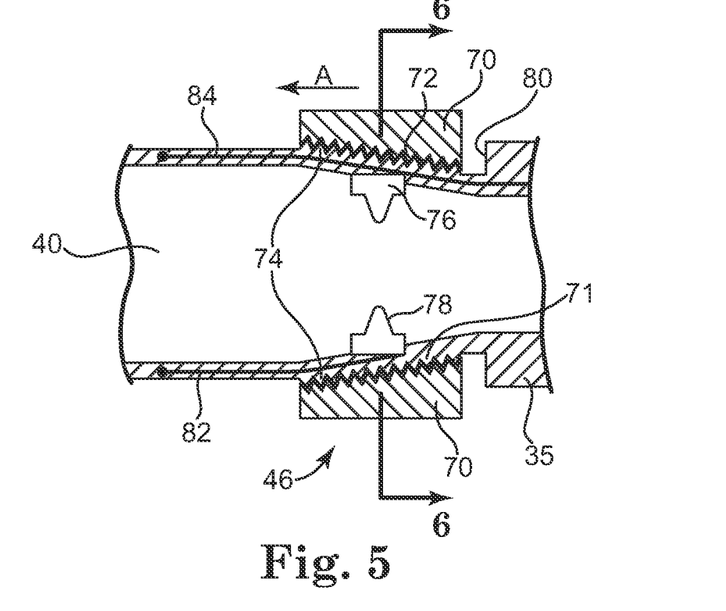
FIG. 5 is a longitudinal cross-section of an adjustable electrical contact of the vascular access system of FIG. 2 according to some embodiments of the present invention.

FIG. 5 shows a medial portion of the hemostasis valve 22 of FIG. 2 according to embodiments of the present invention, including the adjustable electrical contact 46. Although FIG. 5 shows the adjustable electrical contact 46 distal of the optional side access port 42, in some embodiments the adjustable electrical contact 46 is located proximal of the side access port 42. The adjustable electrical contact 46 comprises an actuator 70 and a flexible portion 71 of the hemostasis valve body 35. As shown, the actuator 70 is a barrel adjuster that is rotatable about the flexible portion 71. An outer surface of the actuator 70 is optionally patterned or otherwise provided with a surface that facilitates the gripping of the actuator 70. The inner surface of the actuator 70 shown in FIG. 5 has internal threads 72 formed thereon. In addition, the inner dimension of the actuator 70 tapers distally.

As shown, a portion of the outer surface of the flexible portion 71 of the hemostasis valve body 35 also has external threads 74 formed thereon, and is also tapered distally. The internal and external threads 72, 74 mechanically interact with one another such that rotating the actuator 70 around the hemostasis valve body 35 moves the actuator 70 longitudinally with respect to the hemostasis valve body 35. In other embodiments, the actuator 70 can be moved axially along the hemostasis valve with little or no rotational motion (as opposed to having to rotate the actuator 70 to cause it to move along the hemostasis valve) and the actuator 70 interacts with the hemostasis valve in other ways, for example through a series of clicks or indicators. Further, disposed on an inner surface of the flexible portion 71 of the hemostasis body is one or more adjustable contacts 76 that form inner electrically conductive surfaces 78. The inner electrically conductive surfaces are optionally sharpened (as shown).

The longitudinal movement of the actuator 70 is distally restricted by a stop 80. The stop 80 is a portion of the hemostasis valve body 35 that is radially larger than an inner diameter of the actuator 70, preventing movement of the actuator 70 distal of the stop 80.

As the actuator 70 shown in FIG. 5 is rotated and moved proximally (in the direction of arrow "A"), the distally tapering surface of the actuator 70 exerts compressive force on the distally tapering outer surface of flexible portion 71. The flexible portion 71 of the hemostasis valve body 35 is radially flexible relative to the actuator 70 (compressive forces from the actuator cause the flexible portion to radially compress).

In some embodiments, the flexible portion 71 is a portion of the hemostasis body 35 that comprises a different material and/or a different structure relative to portions of the hemostasis valve body 35 surrounding the flexible portion 71. In other embodiments, the portions of the hemostasis valve body 35 surrounding the flexible portion 71, or optionally the entire hemostasis valve body 35, are radially flexible relative to the actuator 70.

In response to the compressive force from the actuator 70, the flexible portion 71 moves from a first radially expanded configuration to a second radially constricted configuration. This radial movement of the flexible portion 71 causes the adjustable contacts 76 to move from a first radially expanded configuration to a second radially constricted configuration.

In some embodiments, the flexible portion 71 is elastic, and as such, the flexible portion 71 and the adjustable contacts 76 move from the second radially constricted configuration to a third radially expanded configuration when the compressive force from the actuator 70 is removed. The third radially expanded configuration can be the same as the first radially expanded configuration.

It is also noted that the outer surface of the flexible portion 71 and the inner surface of the actuator 70 can both be tapered proximally, rather than distally as shown in FIG. 5. In this instance, advancing the actuator 70 in a direction opposite the arrow "A" will move the flexible portion 71, and the adjustable contacts 76, from a radially expanded configuration to a radially constricted configuration.

Also shown in FIG. 5 are electrical conductors 82, 84. The electrical conductors 82, 84 are electrically coupled to the controller 34 via wires 55. In some embodiments, an electrical coupling (not shown) is disposed between the wires 55 and one or both of the electrical conductors 82, 84. The electrical coupling has a coupled and an uncoupled configuration. In the coupled configuration, the coupling provides an electrical pathway from the controller to one or more of the electrical conductors 82, 84. In the uncoupled configuration, the hemostasis valve is not attached to the controller, which eases manipulation and placement of the hemostasis valve 22.

In some embodiments, and as shown in FIG. 5, the conductors 82, 84 are disposed at least partially within a wall of the hemostasis valve body 35. The conductor 82 extends from a proximal position on the hemostasis valve body 35 through the hemostasis valve wall to electrically connect to one or more adjustable contacts 76. The conductor 84 extends from a proximal position on the hemostasis valve body 35, through the hemostasis valve wall to the connector member 56, which will be further discussed below.

Figure 6:
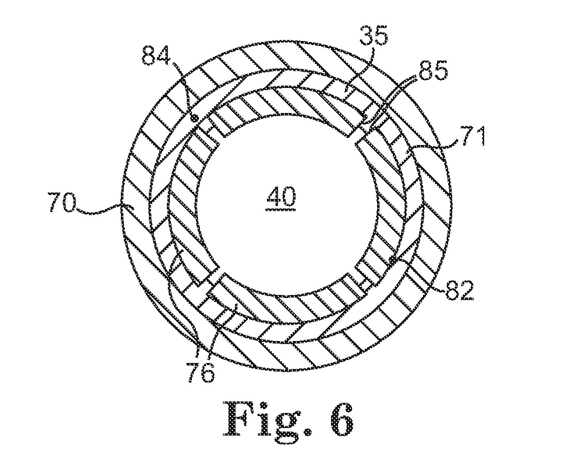
FIG. 6 is a cross-section of the adjustable electrical contact of FIG. 5 according to some embodiments of the invention.

FIG. 6 shows a cross-section of the adjustable electrical contact 46 of FIG. 5 according to some embodiments of the present invention. The adjustable electrical contact 46 has one or more adjustable contacts 76 disposed on the inner surface of the flexible portion 71 of the hemostasis valve body 35. The adjustable electrical contact 46 optionally comprises one or more, two or more, three or more, or four or more adjustable contacts 76.

As shown in FIG. 6, the adjustable contacts 76 have adjacent electrically conductive surfaces 85. As the adjustable contacts 76 are moved from a radially expanded configuration to a radially constricted configuration, the adjacent electrically conductive surfaces 85 are brought closer to one another and, eventually, are electrically coupled to one another. In this way, an electrical signal passed through the conductor 82 can be communicated to or from all of the adjustable contacts 76. Optionally, a separate electrical connection is made between each of the one or more adjustable contacts 76 and the conductor 82.

In alternative embodiments, the adjustable electrical contact 46 comprises a contact 76 that circumnavigates substantially the entire inner circumference of flexible portion 71. In some embodiments, such a contact 76 has a gap formed in one side of the contact 76 and the gap allows the contact 76 to move between a radially expanded configuration and a radially constricted configuration. In yet other embodiments, the contact 76 is a continuous ring of electrically conductive material, and the ring is radially flexible, allowing the ring to move between a radially expanded configuration and a radially constricted configuration.

Figure 7:
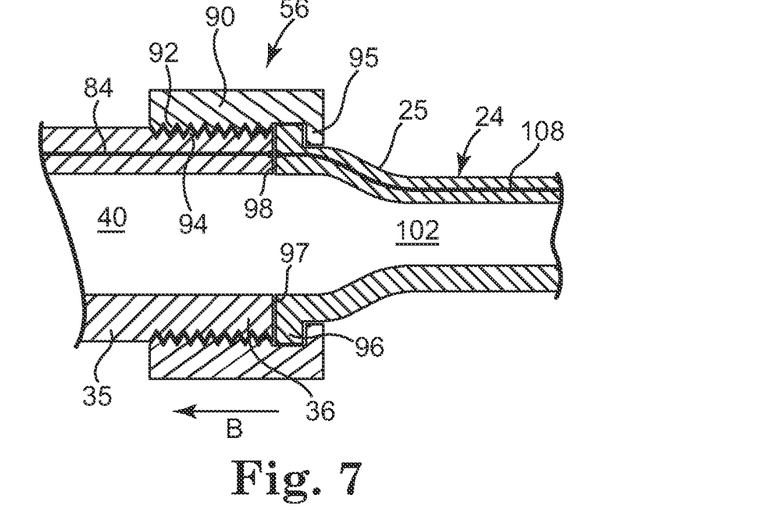
FIG. 7 is a longitudinal cross-section of a connector member of the vascular access system of FIG. 2 according to some embodiments of the present invention.

FIG. 7 shows a longitudinal cross-section of a connector member 56 of the vascular access system 20 according to some embodiments of the present invention. The connector member 56 connects the hemostasis body distal end 36 to the guide catheter proximal portion 25. When connected, the lumen 40 of the hemostasis valve body 35 and a lumen 102 defined by the guide catheter 24 together forms a continuous lumen from the proximal end 38 of the hemostasis valve 22 to the guide catheter distal portion 26.

In some embodiments, and as shown in FIG. 7, the connector member 56 comprises male and female threaded fittings. The hemostasis valve distal end 36 comprises the male threaded fitting, and a female threaded fitting 90 is provided on the guide catheter proximal portion 25. The female fitting 90 has an inner surface with threads 92 formed thereon, and the male fitting has an outer surface with threads 94 formed thereon. The two sets of threads 92, 94 mechanically interact with one another to couple the male and female fittings to one another.

In addition, the female fitting 90 has a first flange 95 and the guide catheter proximal portion 25 has a second flange 96. The hemostasis valve distal end 36 has a distal surface 97 and the guide catheter proximal portion 25 has a proximal surface 98. The first flange 95 mechanically surrounds the second flange 96 such that, when the female fitting 90 is threaded onto the hemostasis valve distal end 36, the guide catheter proximal surface 98 is brought into close proximity with, or brought into contact with, the hemostasis valve distal surface 97.

In other embodiments, the threaded fittings are reversed. The guide catheter proximal portion 25 has the male fitting formed thereon and the female fitting is provided on the hemostasis valve body distal end 36.

Figure 8:
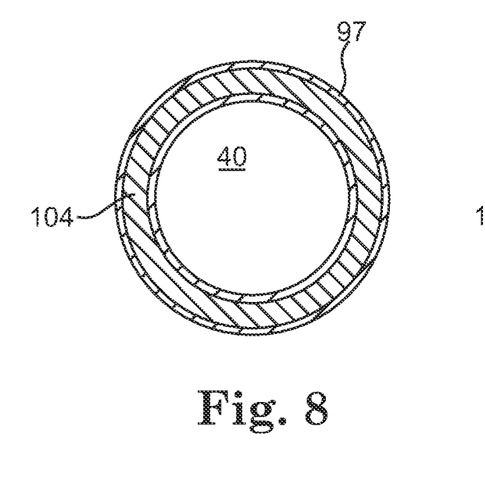
FIG. 8 is an end view of the distal end of the hemostasis valve body of FIG. 7 according to some embodiments of the present invention.

FIG. 8 is an end view of the distal end of the hemostasis valve 40. The hemostasis valve distal surface 97 has one or more distal electrical contacts 104. In some embodiments, and as shown in FIG. 8, the distal electrical contact 104 is a continuous electrically conductive surface, for example formed by a continuous ring of electrically conductive material that is attached to and/or embedded in the hemostasis valve distal end 36. The conductor 84, which was described earlier with respect to FIGS. 5 and 6, extends through a wall of the hemostasis valve body 35 and is electrically connected to the distal electrical contact 104. In other embodiments, the hemostasis valve distal surface 97 has more than one electrical contact 104. In such embodiments, each of the electrical contacts 104 is electrically coupled, either directly or indirectly, to the conductor 84.

Figure 9:
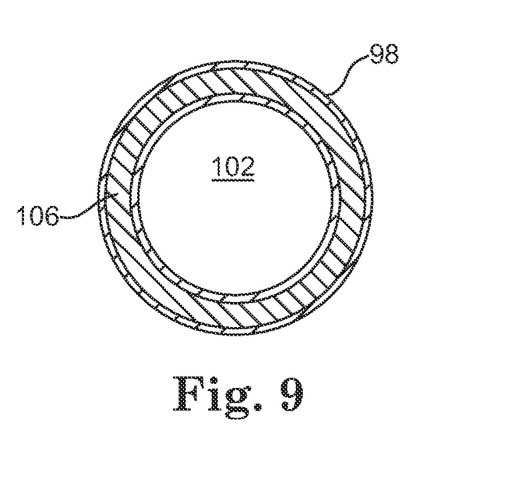
FIG. 9 is an end view of the proximal end of the guide catheter of FIG. 7 according to some embodiments of the present invention.

FIG. 9 is an end view of the proximal end of the guide catheter 24. The guide catheter proximal surface 98 has one or more proximal electrical contacts 106. In some embodiments, and as shown in FIG. 9, the proximal electrical contact 106 is a continuous electrically conductive surface, for example formed by a continuous ring of electrically conductive material that is attached to and/or embedded in the guide catheter proximal portion 25. A guide catheter conductor 108 (shown in FIG. 7) is electrically coupled to the electrical contact 106. In other embodiments, the guide catheter proximal surface 98 has more than one electrical contact 106. In such embodiments, each of the electrical contacts 106 is electrically coupled, either directly or indirectly, to the guide catheter conductor 108.

The conductor 108 extends along a portion of the guide catheter 24, and a distal portion of the conductor 108 is electrically coupled to the guide catheter electrode 28 (not shown in FIGS. 7-9). As such, electrical signals can be passed along an electrically conductive pathway to or from the controller 34, through the hemostasis valve body 35, through the connector member 56, through the guide catheter 24 and to or from the guide catheter electrode 28.

In some embodiments, one or more of the conductors 82, 84, 108 comprise a single solid wire that is disposed at least partially within the wall of the hemostasis valve body 35 or the guide catheter 24. In other embodiments, the conductors 82, 84, 108 are multifilar wires, for example, coiled, cabled, or braided multifilar wires. In yet other embodiments, the conductors 82, 84, 108 can be other conductive members that facilitate the transmission of electrical signals. For example, the guide catheter 24 optionally has a conductive member 108 that comprises a conductive layer of the guide catheter.

In some embodiments, a seal is formed between the surfaces 97, 98 and/or between the contacts 104, 106 in order to prevent pressurized fluids from escaping at the junction between the guide catheter 24 and the hemostasis valve 22. In other embodiments, a sealing member (e.g., an O-ring) is provided on one or both of the surfaces 97, 98. Bringing the surfaces into close proximity to one another, or into contact with one another, causes the sealing member to form a seal between the guide catheter 24 and the hemostasis valve 22.

In some embodiments, a seal is formed between the hemostasis valve 22 and the guide catheter 24 such that the electrically active surfaces 104, 106 are fluidly and electrically isolated from fluids inside (and, in some embodiments, outside) the guide catheter 24 and the hemostasis valve body 35. For example, fluids present within the fluid pathway formed by the lumens 40, 102 are fluidly and electrically sealed from the electrically active surfaces 104, 106 and the other electrical components of the hemostasis valve 22 and the guide catheter 24.

Figure 10A:
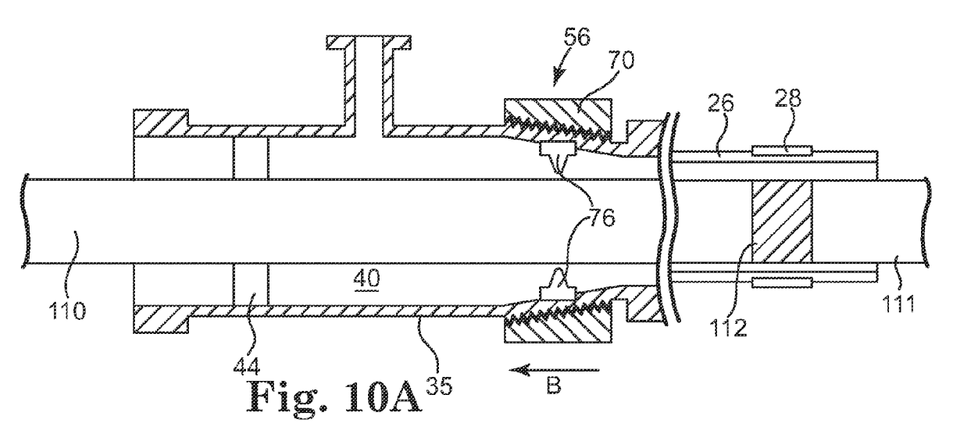
FIG. 10A is a longitudinal cross-section of a hemostasis valve with an elongate medical device disposed therein and an adjustable electrical contact in an open configuration according to some embodiments of the present invention.

FIG. 10A shows a cross-sectional view of a hemostasis valve 22 with a therapeutic system 30 that comprises an elongate medical device 110. The elongate medical device 110 is disposed in the hemostasis valve 22. As discussed above, the hemostasis valve 22 has a body 35 that defines a lumen 40. A valve 44 and adjustable contacts 76 are disposed in the lumen 40. Also as discussed above, the elongate medical device 110 passes through an opening in the valve 44 and the valve 44 forms a complete or partial seal around the elongate medical device 110. The seal completely or partially prevents pressurized fluids from escaping from a patient's body through the hemostasis valve 22.

Figure 10B:
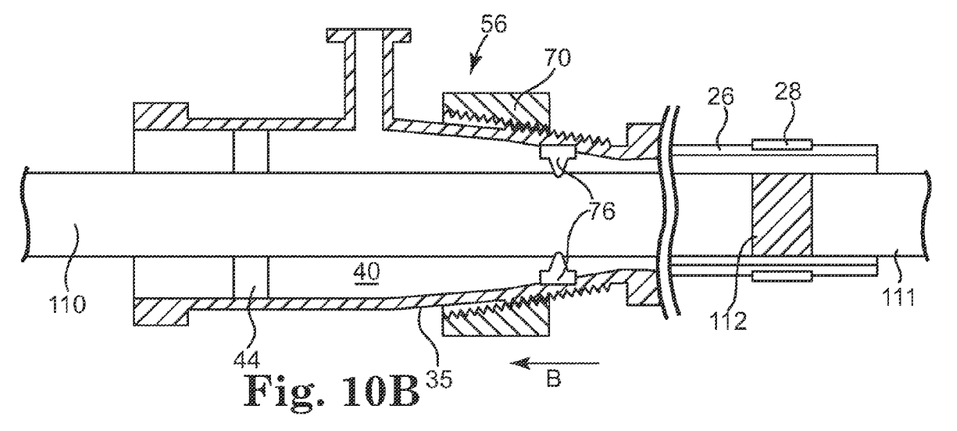
FIG. 10B is the hemostasis valve of FIG. 10A with the adjustable electrical contact in a closed configuration according to some embodiments of the present invention.

The elongate medical device 110 also has a distal end 111 with an electrode 112 disposed thereon. As shown in FIGS. 10A and 10B, the elongate medical device 110 has a length sufficient to extend distally through the hemostasis valve and the guide catheter and exit through the guide catheter distal portion 26.

The elongate medical device also passes through the lumen 40 adjacent the one or more adjustable contacts 76. As shown in FIG. 10A, the radial spacing between the inner surfaces of the one or more contacts 76 when in the expanded configuration is larger than the outer diameter of the elongate medical device 110. This radial spacing is also larger than the inner diameter of the opening in the valve 44.

As described with respect to FIG. 5 above, as the actuator 70 is rotated and moved proximally (in the direction of arrow "B" in FIGS. 10A, 10B), the one or more adjustable contacts 76 are moved between a radially expanded configuration (as shown in FIG. 10A) and a radially constricted configuration (as shown in FIG. 10B). As the adjustable contacts 76 move toward a radially constricted configuration, the adjustable contacts 76 impinge upon, and may eventually protrude into, the elongate medical device 110.

Figure 11:
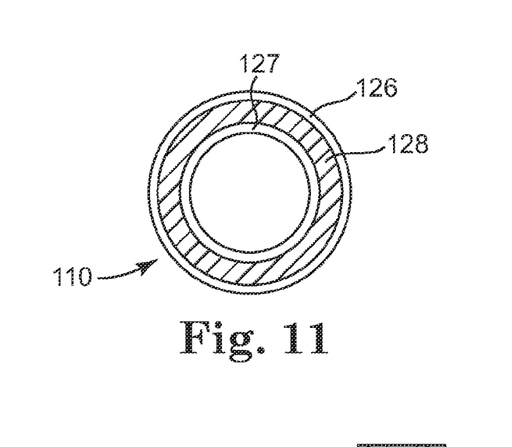
FIG. 11 is a cross-section of an elongate medical device according to some embodiments of the present invention.

FIG. 11 is a cross section of the elongate medical device 110 according to some embodiments of the present invention. As shown in FIG. 11, in some embodiments the elongate medical device 110 is a tubular elongate medical device (e.g., a catheter). The elongate medical device 110 has a first layer of insulation 126, a second layer of insulation 127 and a conductive element or layer 128 disposed between the two insulation layers 126, 127. In some embodiments, the first layer of insulation 126 is an outer layer of the medical device and the second layer of insulation 127 is an inner layer of the medical device. In some embodiments, the conductive element 128 is formed from multiple wires, for example wires in a helical or a braided pattern. In yet other embodiments, one or more elongate conductive elements are disposed in or embedded in a layer of the tubular elongate medical device.

As the adjustable contacts 76 protrude into the elongate medical device 110, the adjustable contacts 76 pierce through portions (e.g., the insulation layer 126) of the elongate medical device 110, making electrical contact with the conductive element. The conductive layer or element of the elongate medical device 110 extends distally to a distal portion of the elongate medical device 110 and electrically connects to the distal electrode 112. As such, electrical signals can be transmitted between the distal electrode 112 and the controller 34.

Figure 12:
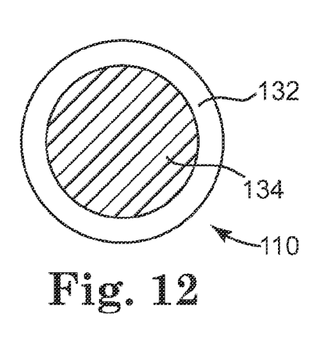
FIG. 12 is a cross-section of an elongate medical device according to some embodiments of the present invention.

FIG. 12 is a cross section of the elongate medical device 110 according to some embodiments of the present invention. As shown in FIG. 12, the elongate medical device 110 has a solid cross-section (e.g., a guide wire with a solid cross-section). The elongate medical device 110 has an insulation layer 132 and a conductive element or core 134. Similar to the embodiment of the elongate medical device 110 shown in FIG. 11, the adjustable contacts 76 pierce the insulation material 132 and make electrical contact with the conductive core 134. The conductive core 134 extends distally to a distal portion of the elongate medical device 110 and electrically connects to the distal electrode 112. As such, electrical signals can be transmitted between the distal electrode 112 and the controller 34.

In yet other embodiments, the elongate medical device 110 is a catheter (e.g., as shown in FIG. 11) or a guide wire (e.g., as shown in FIG. 12) with a portion of the conductive element (e.g., 128, 134) exposed (e.g., uncovered by electrical insulation) along the elongate medical device 110. The exposed conductive element is provided at a predetermined longitudinal position along the elongate medical device 110 such that, when the elongate medical device 110 is disposed at a location at which pacing is being provided, the exposed portion of the conductive element is longitudinally aligned with the adjustable contacts 76. Rather than being required to pierce through insulation to make contact with the conductive element, the adjustable contacts 76 make electrical contact when they impinge on the exposed surface. In some embodiments, all, or substantially all, of the elongate medical device is insulated outside the region of exposed conductive element.

As mentioned above, in some embodiments the elongate medical device is a catheter 110. In such embodiments, a guide wire is optionally used together with the catheter 110. The guide wire is optionally used in an over-the-wire fashion. For example, where FIGS. 10A and 10B show a catheter, the catheter may have a lumen extending from the proximal portion of the catheter to a distal portion of the catheter. The guide wire has a length sufficient to extend through the entire length of the catheter lumen.

Figure 13:
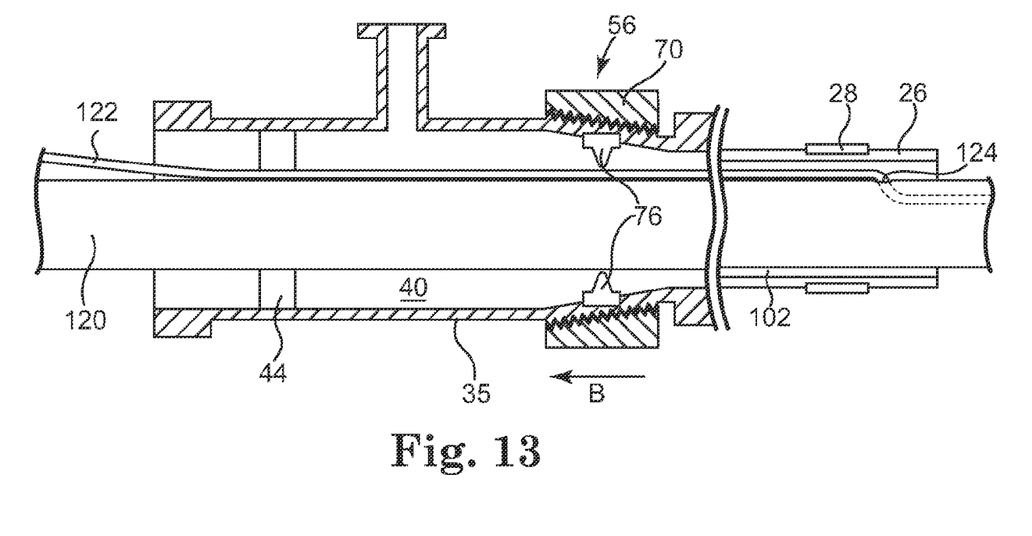
FIG. 13 is a cross-sectional view of a hemostasis valve with a rapid exchange catheter and guide wire disposed therein, with an adjustable electrical contact in an open configuration according to some embodiments of the present invention.

In other embodiments, the catheter is a rapid exchange catheter 120. For example, as shown in FIG. 13, the guide wire 122 extends along the catheter 120 through the hemostasis valve 22 and enters the catheter 120 through a distal port 124. In such embodiments, as the adjustable contacts 76 are moved from a radially expanded configuration to a radially constricted configuration, the adjustable contacts 76 will impinge on both the catheter 120 and the guide wire 122.

In some embodiments, the catheter 120 has a conductive element and a distal electrode, as discussed above with respect to FIG. 11. When the one or more adjustable contacts 76 contacts the conductive element of the catheter 120, electrical signals can be transmitted from the controller 34 to an electrode on the distal end of the catheter 120, similar to electrode 112 shown in FIGS. 10A and 10B.

In other embodiments, the guide wire 122 has a conductive element and a distal electrode, as discussed above with respect to FIG. 12. When the one or more adjustable contacts 76 contacts the conductive element of the guide wire 122, electrical signals can be transmitted from the controller 34 to the electrode on the distal end of the guide wire 122, similar to electrode 112 shown in FIGS. 10A and 10B.

In yet other embodiments, the catheter and the guide wire each have a conductive element and a distal electrode. When the one or more adjustable contacts 76 is moved from a first radially expanded configuration to a second radially constricted configuration, the one or more adjustable contacts 76 impinge upon both the catheter and the guide wire. The one or more adjustable contacts 76 pierce the insulation of one or both of the catheter and guide wire, providing an electrical pathway to one or both of the distal electrodes on the catheter and the guide wire. When the one or more adjustable contacts 76 make electrical contact with conductive elements in both the catheter and guide wire, simultaneous pacing can occur with the electrodes of the guide wire and the catheter.

FIGS. 14A-14D are schematic cut-away views of a coronary artery 140 showing steps of treating a blockage 32 in the coronary artery 140. In a method according to some embodiments of the present invention, a guide catheter is positioned in a coronary ostium (e.g., guide catheter 24 is positioned in a coronary ostium 11 as shown in FIG. 1). The therapeutic system 30 is advanced through the guide catheter and into the coronary artery 140 to the position shown in FIG. 14A. The therapeutic system 30 includes a catheter 146 and a guide wire 148. For example, the catheter 146 is any of the catheters discussed herein and the guide wire 148 is any of the guide wires discussed herein.

Figure 14A:
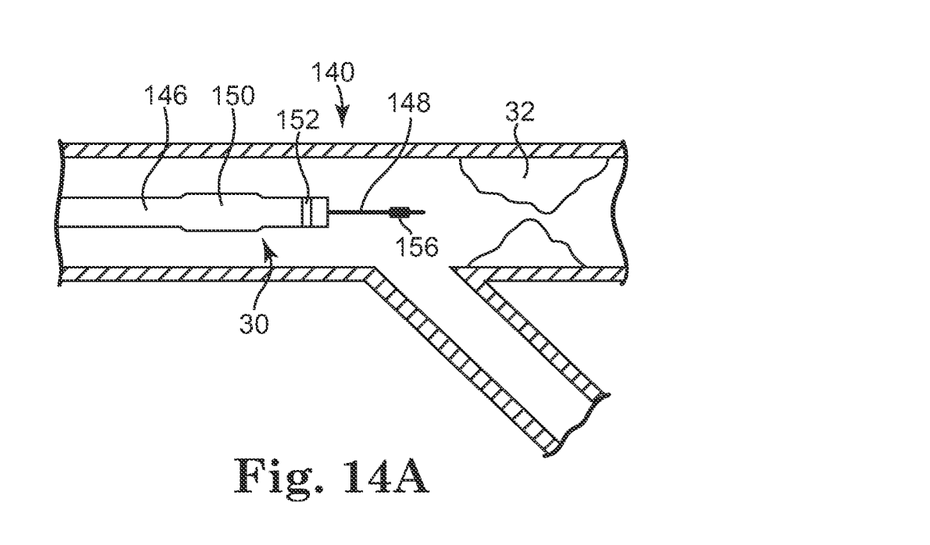
FIGS. 14A-14D are cut-away views of a coronary artery showing the steps of treating a blockage in the coronary artery according to some embodiments of the present invention.

The catheter 146 has a therapeutic device 150 disposed thereon. The therapeutic device 150 is shown in FIG. 14A as a balloon. However, other types of therapeutic devices can be used to treat the blockage, including a stent on a stent delivery balloon, an ablation tool, a snare or other capturing device for capturing the blockage 32, or other devices for treating the blockage. In addition, in some embodiments a balloon or other device for treating the blockage is disposed on the guide wire 148 and the catheter 146 is omitted.

One or more distal electrodes 152 is disposed distal of the therapeutic device 150. Optionally, the electrode 152 is disposed proximal of the therapeutic device 150, or an electrode is placed both distal and proximal of the therapeutic device 150 and both electrodes are connected to a conductive element of the therapeutic system 30. The guide wire 148 also optionally has a distal electrode 156. The therapeutic system 30 has one or more of the distal electrodes 152, 156 that are electrically connected to a pacing controller in order to provide a temporary pacing of a portion of the heart.

Figure 14B:
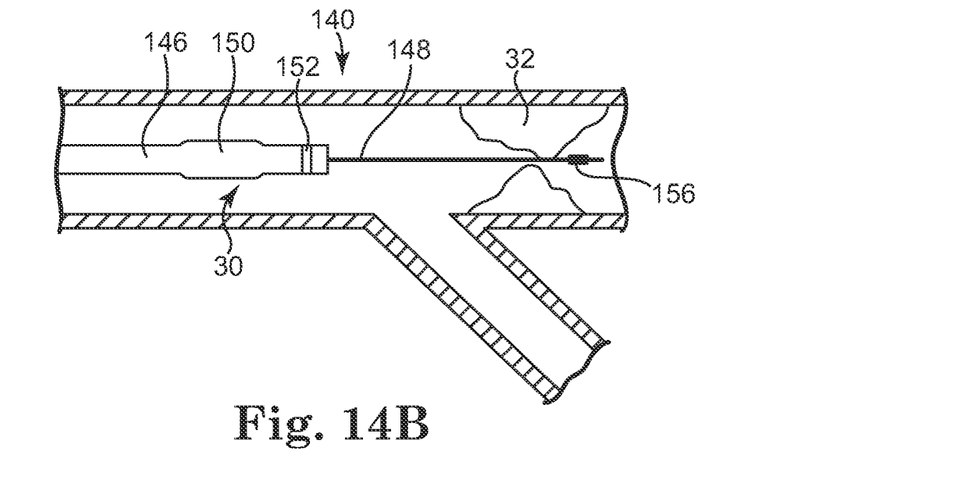

As shown in FIG. 14B, the guide wire 148 is advanced through, and in some instances beyond, the blockage 32. In some embodiments, the blockage completely or mostly occludes the artery, and a distal portion of the guide wire 148 is sufficiently stiff to break through the blockage, creating a channel through which the guide wire 148 and the balloon 150 can pass.

Figure 14C:
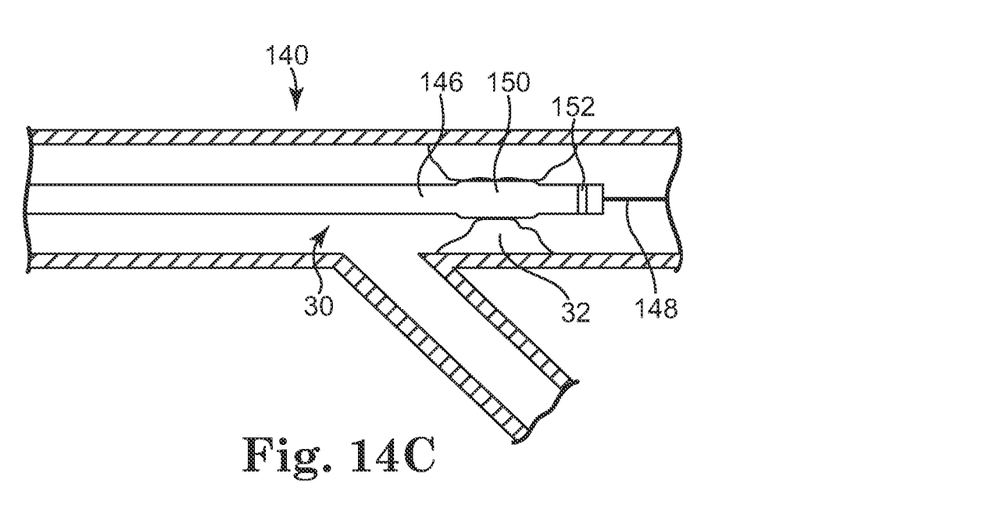
Figure 14D:
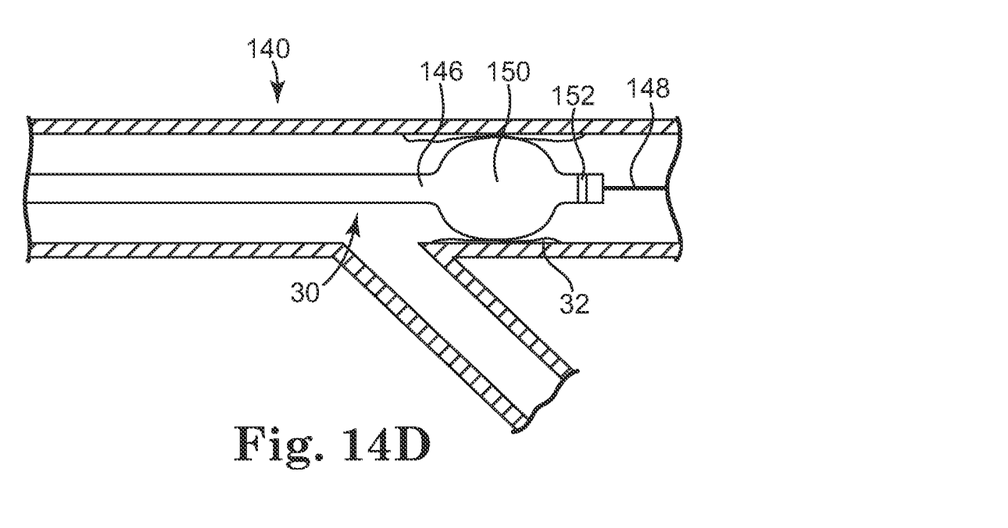

As shown in FIG. 14C, the balloon 150 is advanced along the guide wire 148 to position the balloon 150 within the blockage 32. As shown in FIG. 14D, the balloon 150 is inflated, which causes the blockage 32 to deform, revascularizing the artery 140 and allowing blood to flow more freely through the artery 140. The balloon 150 is deflated and the therapeutic system 30 is removed from the artery 140.

Cardioprotective pacing can be provided during any of the steps shown in FIGS. 14A-14D. In some embodiments, cardioprotective pacing is provided prior to the catheter 146 or guide wire 148 encountering the blockage 32, for example when the catheter 146 and guide wire 148 are positioned as shown in FIG. 14A. In other embodiments, cardioprotective pacing is provided after the guide wire 148 is advanced through the blockage 32, as shown in FIG. 14B. In yet other embodiments, cardioprotective pacing is provided after the balloon or other therapeutic device 150 is staged to treat the blockage 32, as shown in FIG. 14C. In yet other embodiments, the cardioprotective pacing is provided during the treatment of the blockage 32, as shown in FIG. 14D. In yet other embodiments, the cardioprotective pacing is provided after one or both of the catheter 146 and guide wire 148 are removed. In yet other embodiments, the cardioprotective pacing is provided during any combination of the above steps.

In some embodiments, the vascular access system 20 is operated as a bipolar system. In a bipolar system, a first electrode of the vascular access system 20 acts as first pole of the device and a second electrode of the vascular access system 20 acts as a second pole of the device. For example, the electrode on the guide catheter distal portion 26 acts as one pole of the device and one or more of the electrodes 152, 156 on the catheter 146 acts as the other pole of the device.

In other embodiments, the vascular access system 20 is operated as a unipolar system. In a unipolar system, a first electrode disposed on the vascular access system 20 acts as a first pole of the device and a second pole is provided at a remote location in or on the patient's body, for example on an external surface of the patient's body. For example, in some embodiments of the present invention one of the electrodes 152, 156 acts as one pole of the pacing system and the other pole of the pacing system is provided on an external portion of the patient's body.

Figure 15:
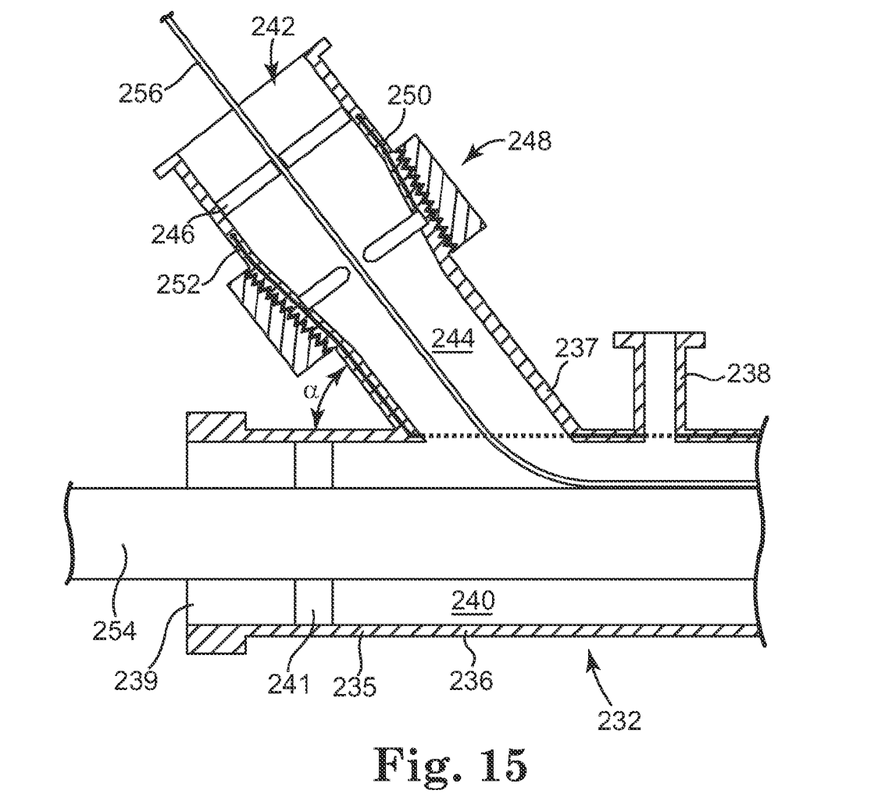
FIG. 15 is a proximal portion of a dual hemostasis valve according to some embodiments of the present invention.

A dual hemostasis valve 232 is shown in FIG. 15 according to some embodiments of the present invention. The hemostasis valve 232 comprises a body 235 with a main body portion 236, a branched body portion 237 and, optionally, a side port 238. The optional side port 238 is similar to any of the embodiments of the side port 42 discussed above. The main body portion 236 defines a proximal port 239 and a distal port (not shown) and defines a main body lumen or passageway 240 that extends from the proximal port 239 to the distal port, similar to the hemostasis body 35. The main body portion 235 has a valve 241 and portions of a connector member (not shown) for connecting to a guide catheter. In some embodiments, the valve 241 has the same structure as any of the valves discussed herein and the connector member has the same structure as any of the connector members discussed herein.

The branched body portion 237 defines a proximal port 242 and a side branch lumen or passageway 244 that extends from the proximal port 242 to the main body lumen or passageway 240. The branched body portion 237 connects to the main body portion 236 in a generally distal direction, or at an angle α which is less than 90 degrees.

The branched body portion 237 has a valve 246 and an adjustable electrical contact 248. In some embodiments, the valve 246 has the same structure as any of the valves discussed herein and the adjustable electrical contact 248 has the same structure as any of the adjustable electrical contacts discussed herein.

Similar to conductors 82, 84, one or more conductors 250, 252 extend through or along the hemostasis valve body 235. For example, conductor 250 extends through the hemostasis valve body 235 to provide an electrical pathway to one or more adjustable electrodes of the adjustable electrical contact 248. Further, conductor 252 extends through the hemostasis valve to provide an electrical pathway to the connector member (not shown). One or more wires (not shown) are connected to the conductors 250, 252, similar to the wires or cables 55 discussed above.

As shown in FIG. 15, an elongate medical device 254 extends through the hemostasis valve main body portion 236, similar to the elongate medical device described with respect to FIGS. 10A and 10B. The elongate medical device 254 can be a catheter (e.g., any of the catheters described with respect to FIG. 11) or a guide wire (e.g., any of the guide wires described with respect to FIG. 12) or any other suitable elongate medical device. In other embodiments, the elongate medical device 254 is a rapid exchange catheter with a guide wire and, as shown in FIG. 13, the catheter and guide wire extend through the hemostasis valve main body portion 236 in a side-by-side fashion.

In addition, a second elongate medical device 256 extends through the branched body portion 237 and into the main body portion 236. In some embodiments, this second elongate medical device 256 is a guide wire, for example any of the guide wires described herein.

Figure 16:
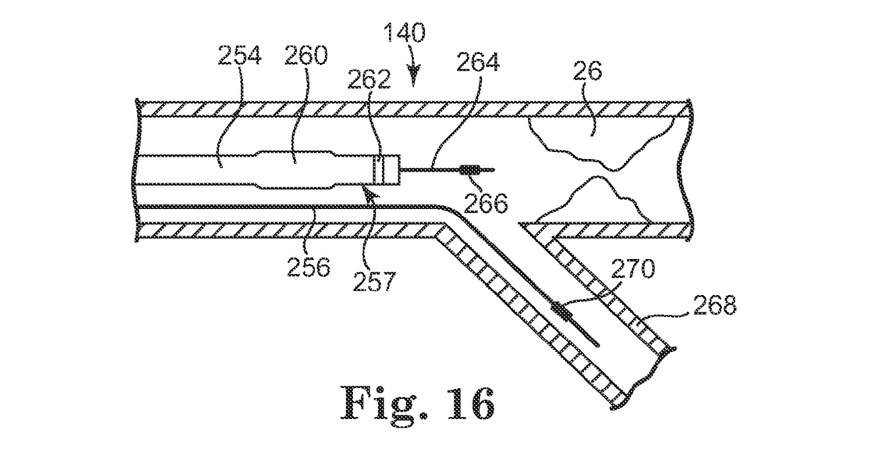
FIG. 16 is a cut-away view of a coronary artery showing a catheter and a first and second guidewire disposed in the coronary artery according to some embodiments of the present invention.

As shown in FIG. 16, a therapeutic system 257 comprises the elongate medical device 254 and optionally includes a guide wire 264. The therapeutic system 257 shown in FIG. 16 has a balloon 260 and an optional distal electrode 262 disposed on the elongate medical device 254. The guide wire 264 optionally has a distal electrode 266. (In other embodiments, the therapeutic system 257 can be any of the therapeutic systems described herein.) The cardiac artery 140 has a side branch 268 and the elongate medical device 256 extends down the main artery 140 and into the side branch 268. The elongate medical device 256 has an electrode 270 disposed on a distal portion thereof.

In other embodiments, the hemostasis valve 232 has a second adjustable electrical contact (not shown) in the main body portion 236. In some embodiments, the second adjustable electrical contact has the structure described above with respect to FIGS. 5 and 6, and the second adjustable electrical contact is located either distal of the optional side access port 238, between the side access port 238 and the branched body portion 237, or proximal of both the side access port 238 and the branched body portion 237. When the dual hemostasis valve 232 has both an adjustable electrical contact 248 and the second adjustable electrical contact in the main body portion 236, the second adjustable electrical contact optionally has a gap or channel in the adjustable electrode and/or in the hemostasis valve body 235 for passage of the elongate medical device 256. When the elongate medical device 256 extends through the gap or channel, moving the adjustable electrical contact in the main body portion to a radially constricted configuration will impinge upon, and eventually pierce portions of, the elongate medical device 254 while not impinging upon, or piercing portions of, the elongate medical device 256. In some such embodiments, one electrical pathway is established through the adjustable electrical contact 248 and the elongate medical device 256 and a second electrical pathway is established through the second adjustable electrical contact and the elongate medical device 254.

Turning again to FIG. 16, in some embodiments the therapeutic system 257 is operated as described above with respect to FIGS. 14A-14D. In addition, the elongate medical device 256 is navigated into the side branch 268 in order to provide a treatment for and/or to provide a pacing signal to the side branch 268. For example, in some embodiments, cardioprotective pacing is provided in the side branch 268 rather than, or in addition to, providing cardioprotective pacing in the vessel 140.

In some embodiments, the vascular access system can be operated in a bipolar manner, with the guide catheter distal electrode (not shown in FIGS. 15 and 16) acting as one pole and one or more of the electrodes 262, 266, 270 acting as the other pole. The cardioprotective pacing can be provided simultaneously through more than one of the electrodes 262, 266, 270, or the system can have the ability to sense which one, or which combination of, the electrodes 262, 266, 270 most effectively provides the cardioprotective pacing and use that electrode or combination of electrodes. Also, in some embodiments, one or both of the electrodes 262, 266 act as one pole of the pacing system and the electrode 270 acts as the other pole of the pacing system.

In addition, in other embodiments the pacing system is operated in a unipolar manner. One or more of the electrodes 262, 266, 270 or the distal electrode disposed on the guide catheter acts as one pole of the pacing system and a second pole of the pacing system is provided at another location in or on the patient's body. In such a unipolar operation, two or more of the electrodes 262, 266, 270 or the distal electrode disposed on the guide catheter can simultaneously provide pacing signals, or the system can determine which one or more electrodes most effectively paces the desired portion of the heart and use that one or more electrode for the pacing procedure. In some embodiments, the cardioprotective pacing is provided during any one or more of the portions of the procedure described above with respect to FIGS. 14A-14D.

Figure 17:
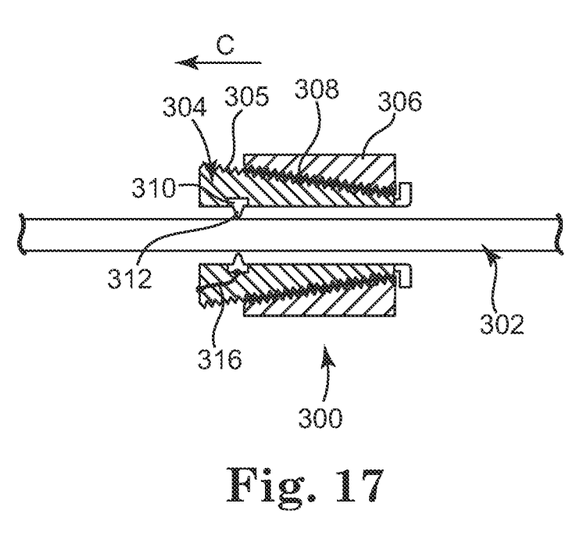
FIG. 17 shows a guidewire with a guidewire torquer disposed thereon according to some embodiments of the present invention.

FIG. 17 shows a cross-sectional view of a torquer 300 according to embodiments of the present invention. The torquer 300 surrounds an elongate medical device 302 (e.g., any of the elongate medical devices described herein). The torquer 300 has an inner member 304 with an outer, threaded surface 305 and an outer member 306 with an inner, threaded surface 308. The threaded surfaces 305, 308 mechanically interact such that turning the outer member 306 with respect to the inner member 304 moves the outer member 306 longitudinally with respect to the inner member 304, similar to the adjustable electrical contacts described herein. One or more adjustable electrodes 310 are disposed on an inner surface of the inner member 304. The one or more adjustable electrodes optionally have a pointed or sharpened portion 312. In some embodiments, the one or more adjustable electrodes 310 are similar to any of the adjustable electrodes described herein.

The inner surface 308 and the outer surface 305 both taper in the same direction, for example distally as shown in FIG. 17. As explained above with respect to the adjustable electrical contacts, rotating the outer member 306 with respect to the inner member 304 moves the outer member 306 with respect to the inner member 304 in the direction of arrow "C," which provides a compressive force on the inner member 304. Inner member 304 is radially flexible with respect to outer member 306, and, in response to the compressive force, the inner member 304 is moved between a radially expanded configuration (as shown in FIG. 17) and a radially constricted configuration. As the inner member 304 is moved to the radially constricted configuration, the adjustable electrical contacts 310 impinge upon, and may eventually pierce through a portion of, the elongate medical device 302, as discussed above with respect to the adjustable electrical contacts. (A portion of the elongate medical device 302 may also have an exposed conductive element, as discussed above.)

Further, the torquer 300 comprises a conductor 316 that provides an electrical pathway from an outer portion of the torquer 300 to the adjustable electrode 310. Similar to the conductors 82 and 250 described above, the conductor 316 can be connected via a wire or cable to a pacing controller. Cardioprotective pacing is provided through the torquer 300 and the elongate medical device 302 to an electrode disposed on a distal portion of the elongate medical device 302.

For example, in some embodiments, a cardioprotective pacing signal is provided through the torquer 300 to one or more of the electrodes 112, 152, 156, 262, 266 and 270.

Where a therapeutic system includes more than one distal electrode (e.g., electrode pair 152, 156 in therapeutic system 30 or electrode pair 262, 266 in therapeutic system 257), the system can provide a separate pacing signal to each of the electrodes. For example, a pacing signal can be provided to both electrodes 152, 156 through a torquer 300, or a pacing signal can be provided to one of the electrodes 152, 156 through a torquer and to one of the electrodes 152, 156 through the hemostasis valve. As another example, a pacing signal can be provided to both electrodes 262, 266 through a torquer 300, or a pacing signal can be provided to one of the electrodes 262, 266 through a torquer and to one of the electrodes 262, 266 through the hemostasis valve.

In some embodiments, therapeutic systems 30, 257 operate in a bipolar mode, for example with one electrode of the therapeutic system being one pole and the other electrode in the pair being the other pole. In other embodiments, the therapeutic systems 30, 257 operate in a bipolar mode with a distal electrode on a guide catheter being one pole and one or both of the electrodes of the therapeutic systems 30, 257 being the other pole.

In addition, in some embodiments the torquer 300 is used to electrically connect a pacing controller to the elongate medical devices 110 and 256 rather than the adjustable electrical contacts shown in FIGS. 10A, 10B and 15.

In some embodiments, when the torquer 300 is in a radially constricted configuration and the adjustable electrodes 312 are contacting a conductive element of the elongate medical device 302, the inner surface of the inner member 304 fits around and is securely attached to the elongate medical device 302. The torquer 300 can be gripped by an operator, providing a larger and more effective grip compared to gripping the elongate medical device 302 itself. In some embodiments, this allows for increased torquability and control and facilitates the placement of the elongate medical device 302. Further, in some embodiments, an electrical coupling (not shown) is disposed between the conductor 316 and a pacing system controller. The electrical coupling has a coupled and an uncoupled configuration. In the coupled configuration, the coupling provides an electrical pathway from the controller to an electrode at a distal end of the elongate medical device 302. In the uncoupled configuration, the torquer 300 is not attached to the controller, which eases manipulation and placement of the torquer 300.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of providing temporary cardioprotective pacing comprising:
   providing a hemostasis valve comprising:
      a valve body including a proximal port and a distal port, the valve body defining a lumen extending between the proximal and distal ports;
      a valve disposed in the lumen, the valve including a resilient material defining an opening, the resilient material being configured to deform and form a seal around a medical device that is extending through the opening; and
      an adjustable electrical contact disposed in the lumen and having an electrically conductive surface, the adjustable electrical contact having an expanded configuration and a constricted configuration;
   disposing a therapeutic system through the opening in the valve and the adjustable electrical contact, the therapeutic system comprising one or more distal electrodes and a conductive element electrically coupled to the one or more electrodes and extending along a portion of the therapeutic system, the valve portion of the hemostasis valve sized and configured to seal around a portion of the therapeutic system;
   disposing a distal portion of the therapeutic system in a cardiac artery;
   moving the adjustable electrical contact from an expanded configuration to a constricted configuration;
   piercing an outer layer of the therapeutic system; and
   making electrical contact with the conductive element;
   providing cardioprotective pacing signals through the hemostasis valve to the electrode.

2. The method of claim 1, wherein the therapeutic system comprises a balloon catheter, the method further comprising the step of using the balloon to treat a blockage in the artery.

3. The method of claim 2, wherein the cardioprotective pacing signals are provided prior to treatment of the blockage.

4. The method of claim 2, wherein the cardioprotective pacing signals are provided during treatment of the blockage.

5. The method of claim 2, wherein the cardioprotective pacing signals are provided after treatment of the blockage.

* * * * *